Figure 1:
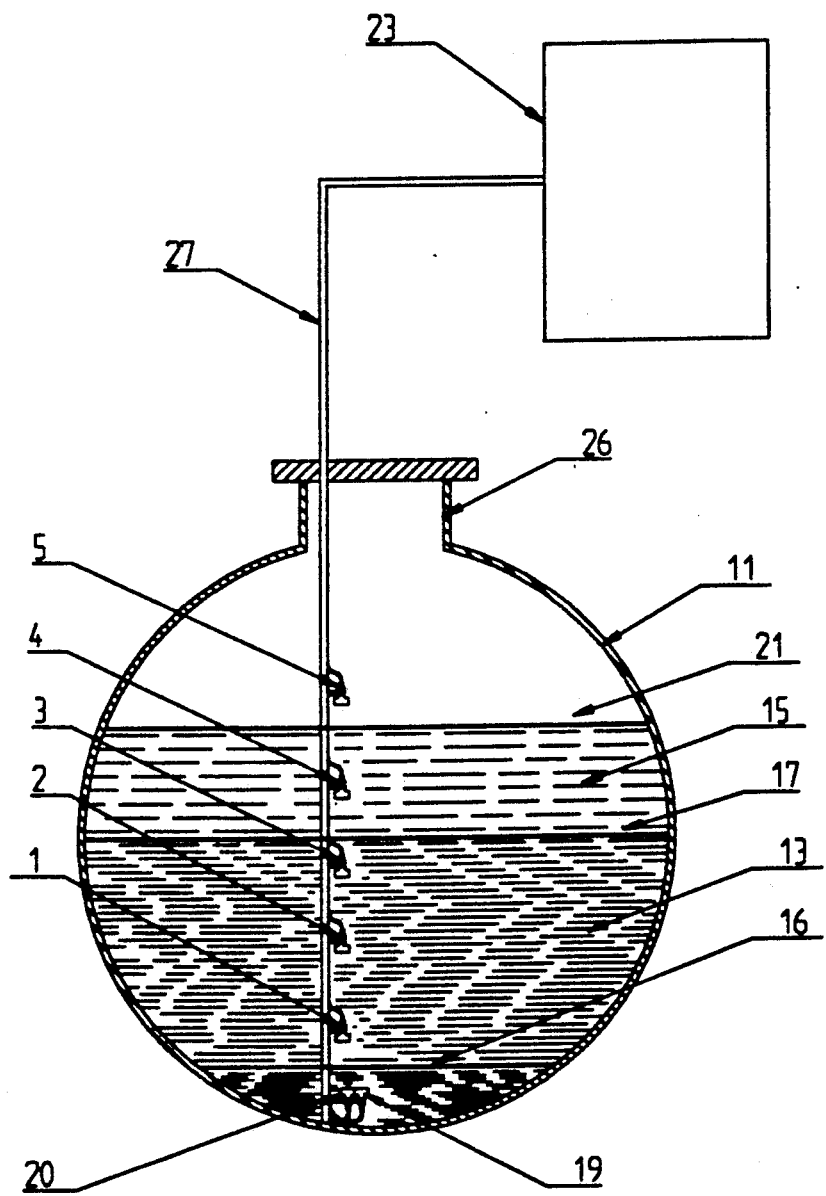

United States Patent [19]

Eriksson

[11] Patent Number: 5,036,703
[45] Date of Patent: Aug. 6, 1991

[54] METHOD AND APPARATUS FOR TESTING LIQUID FILLINGS IN TANKS

[76] Inventor: Bror A. Eriksson, Skattkärrsvägen 36, S-650 10 Karlstad, Sweden

[21] Appl. No.: 482,935

[22] Filed: Feb. 21, 1990

[30] Foreign Application Priority Data

Feb. 23, 1989 [SE] Sweden ................. 8900629

[51] Int. Cl.⁵ .............................. G01F 23/28
[52] U.S. Cl. ..................... 73/290 V; 367/908; 181/402; 181/124
[58] Field of Search ........... 73/290 V; 367/908; 374/117; 181/400, 402, 123, 124, 0.5

[56] References Cited

U.S. PATENT DOCUMENTS

| | | | |
|---|---|---|---|
| 2,883,861 | 4/1959 | Van Valkenburg et al. | 73/290 V |
| 2,990,543 | 6/1961 | Rod | 73/290 V |
| 4,248,087 | 2/1981 | Dennis et al. | 73/290 V |
| 4,320,659 | 3/1982 | Lynnworth et al. | 73/290 V |
| 4,545,245 | 10/1985 | Sharp | 73/290 V |
| 4,635,478 | 1/1987 | Hope | 374/142 |
| 4,675,660 | 6/1987 | Boscolo | 73/290 V |
| 4,748,846 | 6/1988 | Haynes | 73/290 V |
| 4,765,186 | 8/1988 | Dieulesaint et al. | 73/290 V |
| 4,896,535 | 1/1990 | Duckart et al. | 73/290 V |

FOREIGN PATENT DOCUMENTS

| | | | |
|---|---|---|---|
| 2436372 | 5/1980 | France | 73/290 V |
| 0046429 | 4/1981 | Japan | 73/290 V |
| 0222223 | 9/1988 | Japan | 73/290 V |

*Primary Examiner*—William A. Cuchlinski, Jr.
*Assistant Examiner*—Diego F. F. Gutierrez
*Attorney, Agent, or Firm*—Nixon & Vanderhye

[57] ABSTRACT

The invention relates to a method and an apparatus for investigating a filling of liquid in a container, e.g. a fuel tank in respect of actual volume, density, temperature, opacity or other condition. From an emitter (19) at the bottom of the container there are emitted pulses of ultrasonic waves which are reflected by one or more horizontal border faces (17, 21) of the liquid and returned to the bottom of the container and detected by a receiver (20) there. The passage times of the reflected signals are compared with the passage times of direct and not-reflected signals that are detected by a plurality of receivers (1, 2, 3, 4, 5) placed above each other in fixed known positions. The result of said comparison is made the basis of a calculation of the sought quality. Measurement of the passage times, comparison, calculation and exposition of the result takes place by the use of electronic or data equipment (23).

8 Claims, 1 Drawing Sheet

METHOD AND APPARATUS FOR TESTING LIQUID FILLINGS IN TANKS

The invention relates to a method and an apparatus for testing a liquid filling in a container, such as a fuel tank.

In order to determine the position of a liquid level it is previously known to have a radiation source emit a pulse of an ultra sonic ray which, after having passed through the liquid and having been reflected against the lower side of the free surface of the liquid, is sent back to a receiver placed at the container bottom and close to the radiation source.

The time needed for the ultrasonic pulse to move up and down through the liquid is measured and gives an indication of the level of the reflecting surface above the container bottom.

Several methods for achieving the objective are previously known, all of which are deficient and of little accuracy because they do not take into account that the transmission velocity of the ultrasonic waves in the liquid varies with certain characteristics of the liquid, which may differ between liquid layers having mutually different constitution, temperature or other characteristics. It has been proposed to obtain better accuracy by comparing the passage time of pulses reflected by the surface of the liquid with the passage times of pulses reflected by a number of reflectors placed at fixed known levels in the container. However, this method is not secure due to the risk of confusing the various echoes.

The risk is particularly apparent when the liquid is layered, so that there are more than one reflecting liquid face (also referred to herein as a border face).

The present invention relates to an improvement of the measuring accuracy obtained in principle by comparing the passage time of pulses having been reflected with passage times of pulses having passed through the liquid in one direction only. The characteristic features of the invention are more clearly set forth in the following detailed description, and details of preferred solutions are also described herein below with reference to the accompanying drawing, in which FIG. 1 diagramatically shows an apparatus for performing the method of the invention.

In the drawing, 11 designates a container or tank, holding fuel oil or crude oil at a tap station or a distribution center, where it is important to have a reliable control of the liquid contents, and particularly an accurate knowledge of its actual volume. In the drawing it is assumed that the tank 11 has a lower filling or layer 13 of heavier oil and an upper filling or layer 15 of somewhat lighter oil, and it is also assumed that the two layers have not been mixed, so that there is a defined border face 17 between them. The reason for this may be that they are of different origin or have been added on different occasions or are of different temperatures. A second border face 16 may be formed between the oil and the dirty water collected at the bottom of the tank.

According to the invention, the filling or contents of the tank are examined by the use of ultrasonic sound energy omitted from a emitter 19 placed inside the tank and upon its bottom. Short pulses of ultrasonic waves are emitted with periodic interruptions from said emitter, and are directed upwardly within a narrow space angle. These pulses are reflected partly by the border face 17, and partly by the free liquid surface 21, and are then directed back downwardly to the bottom of the tank, where they are received by a receiver 20. The receiver 20 may be a separate element or may be combined with the emitter 19. The combination may comprise a crystal of some kind, by which an electric current is transformed into mechanical vibrations which are then transferred to the liquid, and vice versa.

Numeral 23 designates a measuring and controlling unit, which is connected by wires in the tube 27 to the emitter 19. Current sent through said wires feed the emitter 19 and control the exact moments of emission of ultrasonic pulses therefrom. The receiver 20 receives the reflected sound pulses (echoes) and transforms them into electric signals which are sent through wires in the tube 27 to the measuring unit 23, wherein the time difference between the moment of emitting ultrasonic pulses and the moment of receiving the corresponding reflected pulses (echoes) from the faces 17 and 21 is established and registered. Knowing the transmission speed of the sound waves, the time difference gives a rough indication of the levels of the reflecting liquid faces above the bottom of the container.

However, the transmission speed of the ultrasonic waves varies with temperature, viscosity etc. of the liquid, and the figures thus obtained are not fully reliable. According to the present invention a stricter accuracy is obtained by relating said time differences to values obtained by a separate investigation or probing of the liquid filling or contents which may disclose possible layer formation, temperature variations or such other inhomogenities of the liquid as will affect the propagation of the sound waves.

The additional equipment required to achieve this objective—which in many respects functions as an independent level probing device—forms a reference means comprising a plurality of mutually equal receivers (upper receivers) 1, 2, 3, 4 and 5 located in fixed positions vertically above each other and along a line coinciding with or running close to the path of the ultrasonic waves or rays emitted from the emitter 19, so that the receivers are successively hit by parts of said rays. The upper receivers 1, 2, 3 and 4 are preferably attached to a probe stick extending vertically from a tank inspection orifice 26 to the bottom of the tank. In the drawing the probe stick forms a part of the tube 27 enclosing the wires connecting the transmitter 19 and all receivers (20, 1-5) to the control unit 23. As an alternative, the receivers 1-5 may be attached to a chain or similar device suspended along the entire height of the tank. The number of upper receivers may be greater than shown and the distances between them may also vary, but this is not required. The distances between them and to the tank bottom are accurately measured metrically and registered in the control unit 23. The volume of each stratum bordered by parallel planes extending through neighbouring receivers is calculated from the measurements of the tank, or may be ascertained when filling the tank by accurately measuring the quantities having been pumped-in at the moments when the respective receivers are successively drowned in the rising liquid.

When the receivers 1-5 are hit by a wave pulse emitted by the emitter 19, they send electric signals to the unit 23, wherein their time lags relative to each other and to the moment of emission of the pulse by the emitter 19 are measured. In all instances the measurement is taken at the steep front of the first period of the interrupted oscillations. The transmission speed of the waves passing between any two receivers is their mutual known metric distance divided by the time difference between their response to the sonic pulse. The magnitude of the speed so calculated discloses certain qualities of the liquid, such as its density; the mutual relation can be found empirically. If, the speed is different in strata of different locations this may be due to different temperatures, which thus will be detected and estimated, or by inhomogenities of other kinds.

The three properties: transmission speed, density and height of a liquid stratum, are dependent upon each other, so that if two of them are known, the third property may be calculated.

If the described equipment is completed with means for measuring the temperature at different levels, other qualities of the liquid and variations thereof can also be detected.

The wave pulses detected by the receivers 1 to 5 have passed through the same strata as have been penetrated twice by the pulse reflected by the surface 21 of the liquid and returned to the receiver 20, and therefore the transmission time of a pulse received by any of the upper receivers 1 to 5 is equal to half the transmission time of an imaginary pulse having been reflected at the corresponding level and received by the low receiver 20. The measurements by the receivers 1-5 are not exposed to disturbances, such as by stray reflections, and will not be influenced by echoes from the reflecting faces of the liquid, which means a great advantage in comparison to known methods.

In the control unit 23 there is performed by known data equipment, including i.a. time basis generators, memories, calculators etc. a registration and reworking of the signals put in from the the receivers 20 and 1-5. A fictitious time scale is formed, on which there are marked the moment of sending a starting signal to the emitter 19 and the moments of receiving the signals from the receivers 1-5. Thus the distances between said marks correspond to the transmission times of sound waves directly received by the receivers 1-5 without reflections. A separate and parallel time scale is also formed, on which are marked the moment of the starting signal to the emitter 19 and the moment of receipt of the echoes by the receiver 20. Then the two time scales are laid parallel and compared. Previous to said comparison the last-mentioned scale should be shrinked in the proportion one to two, i.e. be halved, or the first-mentioned scale should be magnified in the proportion two to one, i.e. be doubled. The time position of each echoe will then appear opposite the markings caused by the receivers 1-5 and can be read off from the first-mentioned scale, where the markings correspond to metrically measured true levels. The result obtained is the level of the sought face of the liquid and can be shown either graphically or numerically on the unit 23.

Due to the presence of the several receivers 1-5 it is possible to ascertain the passage times of of the ultrasonic waves in the liquid strata lying between each pair of receivers and thereby get knowledge of varying qualities of the liquid along the height of the tank, such as temperature, density etc. having influence upon the speed of ultrasonic waves.

Of course, the descibed method and the apparatus for performing the same can be modified in several respects within the limits of the following claims. This applies especially to the functions of the measuring and controlling unit 23, where modern computer techniques offer many possibilities of calculating time differences and graphically or numerically displaying the results.

I claim:

1. A method for determining the level of an upper free surface of a liquid within a container and any horizontal border faces between adjacent layers of liquid in the container, the method comprising the steps of:
   (a) emitting ultrasonic wave pulses from an emitter located in a bottom portion of the container upwardly through the liquid so that echoes of said wave pulses are reflected by said upper free surface and said horizontal border faces and returned for reception by a first receiver located proximate said emitter;
   (b) measuring time between the emitting of said ultrasonic wave pulses from said emitter and reception of corresponding echoes by said first receiver;
   (c) providing a plurality of additional receivers at predetermined levels above said bottom portion of the container such that at least some of said ultrasonic wave pulses are received directly within said plurality of additional receivers;
   (d) measuring time between the emitting of said ultrasonic wave pulses from said emitter and direct reception by each of said plurality of additional receivers; and
   (e) comparing the times measured in steps (b) and (d) and converting differences therebetween into one or more length measures indicative of levels of said upper free surface and said horizontal border faces within said container, and displaying said length measures.

2. The method according to claim 1 wherein the comparing step recited in step (e) is made after first having divided the time measured in step (b) by two.

3. The method according to claim 1 wherein the comparing step recited in step (e) is made after first having multiplied the time measured in step (d) by two.

4. Apparatus for determining the level of an upper free surface and any intermediate horizontal border faces of a liquid within a container comprising: an emitter for intermittently emitting a plurality of ultrasonic wave pulses from a bottom portion of the container; a first receiver located proximate said emitter for receiving ultrasonic wave pulses reflected by the upper free surface of the liquid and any horizontal border faces present within the liquid; a plurality of second receivers placed at predetermined levels within said container above the bottom portion of the container for directly receiving wave pulses emitted by said emitter; and, measuring and controlling means connected to the emitter and to said first and second receivers for measuring and making a comparison of passage times of reflected pulses received in said first receiver and pulses received directly by said plurality of second receivers and including means for displaying results of said comparison as a length measure indicating location of said upper free surface of said liquid and any horizontal border faces within said liquid.

5. Apparatus according to claim 4 wherein said second plurality of receivers comprises five receivers arranged in substantial vertical alignment within said container.

6. Apparatus according to claim 5 wherein one of said five receivers is located above said upper free surface of said liquid.

7. Apparatus according to claim 4 wherein said emitter and said first and second receivers are electrically connected to said measuring and controlling means by wires enclosed in a tube, and wherein said plurality of second receivers are mounted on said tube.

8. A method of examining liquid contents of a container by the utilization of ultrasonic waves, comprising the steps of:
   (a) sending ultrasonic wave pulses through the liquid contents from an emitter in a bottom portion of the container such that said waves reflect from any horizontal border faces within the liquid contents as well as from an upper free surface of the liquid and are returned to a first receiver located proximate said emitter;
   (b) measuring and recording passage times of said wave pulses reflected by said horizontal border faces and said upper free surface and returned to said first receiver;
   (c) locating a plurality of additional receivers within said container at predetermined locations where said additional receivers directly receive at least some of said ultrasonic wave pulses emitted from said emitter;
   (d) measuring and recording passage times of said ultrasonic wave pulses received directly by said additional receivers; and
   (e) comparing the passage times recorded in steps (b) and (d) and displaying results of the comparison as length measures indicative of levels of said upper free surface and said horizontal border faces within the container.

* * * * *